United States Patent [19]

Kniskern et al.

[11] 4,264,764
[45] Apr. 28, 1981

[54] MENINGITIS VACCINE

[75] Inventors: Peter J. Kniskern; Arpi Hagopian, both of Sayreville; Dennis J. Carlo, Middlessex, all of N.J.

[73] Assignee: Merck & Co., Inc., Rahway, N.J.

[21] Appl. No.: 78,430

[22] Filed: Sep. 24, 1979

Related U.S. Application Data

[63] Continuation-in-part of Ser. No. 2,818, Jan. 12, 1979, abandoned.

[51] Int. Cl.³ .............................................. C07G 3/00
[52] U.S. Cl. ..................................... 536/1; 424/88; 424/92; 424/180; 536/117
[58] Field of Search ................... 424/85, 92, 88, 180; 536/1, 117

[56] References Cited

PUBLICATIONS

Norden, C. W., J. of Pediatrics, vol. 80(2), 209–214, 1972.
Felton, L. D., J. of Immunology, vol. 74, 17–26, 1955.
Smith, D. et al., J. of Clin. Invest., vol. 49, 90a, 1970.
Robbins, S. et al., Pediatrics Research, vol. 40, 376 (1970).

*Primary Examiner*—Johnnie R. Brown
*Assistant Examiner*—Blondel Hazel
*Attorney, Agent, or Firm*—Donald J. Perrella; Theresa Y. Cheng; Julian S. Levitt

[57] ABSTRACT

A high molecular weight capsular polysaccharide from *H. influenza* type b is an effective immunogenic agent against infection caused by the *H. influenza* type b bacterium.

1 Claim, No Drawings

MENINGITIS VACCINE

RELATED APPLICATION

The present application is a continuation-in-part of co-pending application Ser. No. 002,818 filed on Jan. 12, 1979.

BACKGROUND OF THE INVENTION

*Hemophilus influenza* type b is the most important cause of bacterial meningitis in children between the ages of 3 months and 4 years. The effect of bacterial meningitis in infants and young children can be severe and may include pyarthrosis, epiglottitis, maxillary sinusitis, ethmoid sinusitis, pneumonia and otitis media. Pyarthrosis in infants is difficult to diagnose and can lead to irreversible damage in the advanced lesion stage; epiglottitis can occur as a result of bacteremia and a tracheotomy is usually mandatory because of the high probability of sudden death as a result of respiratory or cardiac arrest; maxillary sinusitis may remain in a chronic condition for months if untreated while ethmoid sinusitis is very acute leading to periorbital cellulitis in one or both eyes. Pneumonia and otitis media can occur also as a consequence of nasopharyngeal involvement. The possibility of a synergistic effect of bacteria plus virus may exist and untreated cases may terminate fatally. Despite the effectiveness of certain antimicrobial therapy, no decline in mortality has been observed during the last decade to type b-induced meningitis while recovery from the disease has imposed a high percentage of neurological impairment. Clinically, there appears to be an increase in the number of infants under 2-3 months of age who are susceptible as well as in older children; increased adult susceptibility also may be a problem.

OBJECTS OF THE INVENTION

It is, accordingly, an object of the present invention to provide a vaccine which is effective against *H. influenza* type b. Another object is to provide an antigenic and immunogenic high molecular weight capsular polysaccharide from *H. influenza* type b. A further object is to provide compositions for administering the antigenic and immunogenic high molecular weight capsular polysaccharide as a vaccine. Still another object is to provide a method for preparing the antigenic and immongenic high molecular weight capsular polysaccharide. These and other objects of the present invention will be apparent from the following description.

SUMMARY OF THE INVENTION

A high molecular weight capsular polysaccharide from *H. influenza* type b is an effective immunogenic agent against infection caused by the *H. influenza* bacterium. Substantially all of the polysaccharide has a molecular weight of at least about 5,000,000 daltons and about half of the polysaccharide has a molecular weight of about 10,000,000 daltons.

DETAILED DESCRIPTION

The present invention is directed to a high molecular weigh capsular polysaccharide prepared from an encapsulated strain of *H. influenza* type b. Substantially all of this capsular polysaccharide is composed of high molecular weight polysaccharide. Substantially all of the polysaccharide has a molecular weight of at least about 5,000,000 daltons and about half of the polysaccharide has a molecular weight of at least about 10,000,000 daltons. The polysaccharide of the present invention consists of about equal parts of ribose, ribitol and phosphate, and has the general formula

[Ribose-Ribitol-PO$_4$]$_n$

The high molecular weight capsular polysaccharide of the present invention is obtained from an encapsulated strain of *H. influenza* type b. A culture of the organism is grown under suitable conditions in a nutrient medium. After completion of the fermentation the cell paste is removed, e.g., by centrifugation and the remaining fluid is treated to precipitate unwanted proteins, nucleic acids and lipopolysaccharides. A low concentration, i.e., up to about 0.1% of cetrimonium bromide is suitable for this precipitation. The precipitates are removed, e.g., by centrifugation, and the supernatent fluid is concentrated to about one-tenth or less of the original volume. Preferably, the concentration is effected by ultrafiltration whereby low molecular weight contaminants, i.e., below about 50,000 molecular weight are also removed.

A water-miscible alcohol is added to the concentrated liquid to precipitate nucleic acids and other alcohol insoluble contaminants. The alcohol is preferably ethanol which is added until the ethanol concentration is from about 9.5% to about 10.5% (vol/vol), thereby precipitating nucleic acids and other alcohol insoluble contaminants. The precipitates are removed and discarded. An additional quantity of a water miscible alcohol is added to the concentrated liquid to precipitate the high molecular weight capsular polysaccharide of the present invention. The alcohol is preferably ethanol which is added until the ethanol concentration to from about 19% to about 21% (vol/vol) thereby precipitating the high molecular weight capsular polysaccharide of the present invention.

The alcohol-containing liquid is separated from the precipitated polysaccharide, e.g., by centrifugation, filtration, settling, aspiration or other suitable means, and the latter is extracted with an aqueous solution of CaCl$_2$, typically in a concentration of from about 0.1 M to about 2.0 M preferably about 1.0 M to enhance separation of the capsular polysaccharide from impurities. A water-miscible alcohol, preferably ethanol in concentration from about 9.5% to about 10.5% (vol/vol) is added to the CaCl$_2$ extract thereby precipitating any remaining nucleic acids and other alcohol insoluble contaminants. The alcohol-containing liquid is separated from the precipitates, e.g., by centrifugation, filtration, settling, aspiration or other suitable means. The precipitates are discarded. Any lipid-like floating material in the liquid is removed by any suitable means, e.g., by filtering the liquid or by decanting it through cheese cloth. An additional quantity of a water-miscible alcohol, is added, preferably ethanol to a concentration above about 50% (vol/vol), most preferably to from about 70 to about 80% (vol/vol) thereby precipitating the high molecular weight capsular polysaccharide of the present invention.

The precipitate is separated from the alcohol-containing liquid, e.g. by filtration or centrifugation, washed and dried. The dried product is resuspended in sodium acetate solution, pH 6.5-7.4, and extracted with phenol to remove any residual protein contaminants. The aqueous phase is treated, e.g. by dialysis or dilution, to reduce the phenol concentration to below about 1%. To the treated aqueous phase, $CaCl_2$ is added to a concentration of from about 0.01 M to about 0.1 M, preferably about 0.05 M, followed by slow addition of a water-miscible alcohol, preferably ethanol to a final concentration of above 50% (vol/vol), most preferably to from about 70 to about 80% (vol/vol) to precipitate the capsular polysaccharide. The resulting precipitate is collected, washed and dried.

The dried material is resuspended in a dilute aqueous solution of $CaCl_2$, typically from about 0.01 M to about 0.1 M, preferably about 0.05 M, and centrifuged (at about $100,000 \times G$) until over half of the protein and endotoxin contaminants are contained in a glassine pellet. The pellet is discarded and a water-miscible alcohol is added slowly to the supernatant liquid. Preferably the alcohol is ethanol added in quantity effective to raise the ethanol concentration to above 50% (vol/vol), preferably to from about 70 to about 80% (vol/vol). The resulting precipitate is collected, e.g., by centrifugation, filtration or decanting, and washed and dried.

The dried material is resuspended in a dilute aqueous solution of $CaCl_2$, typically from about 0.01 M to about 0.1 M, preferably about 0.05 M, and a water-miscible alcohol is added slowly to the solution. Preferably the alcohol is ethanol which is added in quantity effective to raise the final concentration of ethanol to from about 9 to about 11% (vol/vol). The mixture is clarified by centrifugation at about $100,000 \times G$ and the pellet is discarded. Additional water-miscible alcohol is added, preferably ethanol, in quantity effective to bring the ethanol concentration above 50% (vol/vol), preferably to from about 70 to about 80% (vol/vol). After complete precipitation, the polysaccharide precipitate is collected by centrifugation, and washed and dried.

Pharmaceutical compositions for administering the antigenic and immunogenic high molecular weight polysaccharide as a meningitis vaccine can be prepared by dissolving the purified polysaccharide in a physiologically acceptable medium such as isotonic saline or PBS (phosphate buffered saline) solution which may contain an appropriate amount of a preservative such as thimerosal or phenol according to methods known in the art.

The vaccine so prepared can be used in single dosage or multiple forms to afford sufficient protection against infection caused by the H. influenza bacterium in humans, especially in children. The single dosage level is from 10 $\mu$g to 100 $\mu$g, preferably 25-50 $\mu$g for adults; 10-25 $\mu$g for children.

Following two such injections given at two to eight week intervals, preferably four weeks, protective immunity can be sustained for up to two years.

The following examples illustrate the present invention without, however, limiting the same thereto. All temperatures are expressed in degrees Celsius.

EXAMPLE 1

A culture of a pathogenic isolate of H. influenza type b, e.g., Ross strain, is grown in a medium in which yeast extract dialysate is used in place of whole yeast extract. After the fermentation is completed, the cell paste is removed by Sharples centrifugation and to the supernatent fluid (180 liters) there is added cetrimonium bromide to a concentration of 0.1 weight %. The resulting precipitate is removed by a second Sharples centrifugation at 45,000 rpm ($60,000 \times G$) at 20° and discarded. The supernatant fluid is collected and concentrated at 4° C. on an Amicon DC-30 unit with XM-50 (50,000 Daltons cut-off) hollow fiber cartridges (4.5 $m^2$ membrane area; 2.0 lmp air flow at 20 psi; concentration=10 liters/hour). After 24 hours the original 180 liters of supernatant fluid are reduced in volume to 10.0 liters of retentate. The filtrate is discarded.

To the XM-50 retentate (10.0 liters), 1.11 liters of 100% ethanol is added dropwise with stirring at 4° to a final concentration of 10% ethanol by volume. The mixture is allowed to stir 2-3 additional hours and to stand 12-18 hours at 4° to insure complete precipitation. The supernatant fluid is collected by aspiration and finally by centrifugation in the Beckman J-21B at $11,000 \times G$ (8,000 rpm in the JA-10 rotor) for 30 minutes at 4°. The insoluble pellet is discarded. To the 10% ethanol soluble fraction (11.0 liters) 1.375 liters of 100% ethanol is added dropwise with stirring to a final concentration of 20% by volume. The mixture is allowed to stir 2-3 additional hours and to stand 12-18 hours at 4° to insure complete precipitation.

The resulting 10% ethanol soluble, 20% ethanol insoluble precipitate is collected by centrifugation in the Beckman J-21B at $11,000 \times G$ (8,000 rpm in the JA-10 rotor) for 30 minutes at 4°. The 20% ethanol supernatant fluid is discarded and 30.0 g of the resultant viscous precipitate (Yield, 45.0 g), is mixed with 170.0 ml cold glass-distilled $H_2O$ and 200.0 ml of cold 2 M $CaCl_2.2-H_2O$ is added. The mixture (final concentration=1.0 M $CaCl_2$) is extracted in an ice:water bath at setting No. 2 in the Omnimixer for 30 minutes. Finally, an additional 100.0 ml of 1 M $CaCl_2$ is added and extraction continued for 15 minutes longer. The $CaCl_2$ extract (500 ml) is brought to 10% ethanol by adding 55.5 ml of 100% ethanol dropwise with stirring at 4°. After additional stirring for 2-3 hours, the mixture is allowed to stand 12-18 hours at 4° to insure complete precipitation. The mixture is centrifuged in the Beckman J-21B at $11,000 \times G$ (8,000 rpm in the JA-10 rotor) for 30 minutes at 4°. The supernatant fluid is decanted through cheese cloth to remove lipid-like floating material. The insoluble pellet is discarded and the 10% ethanol soluble supernatant fluid (500 ml) is brought to 75% ethanol by adding 1,300 ml of 100% ethanol dropwise with stirring over a 2-3 hour period. The mixture is then allowed to stand 12-18 hours at 4° to insure complete precipitation.

The resulting insoluble precipitate is recovered on a Buchner funnel with a medium glass fritted disc (pore size 10-15 microns), washed three times with 100% ethanol (250 ml per wash) and three times with acetone (250 ml per wash). All washes are discarded. The insoluble product is dried in vacuo over anhydrous $CaCl_2$ at 4°. The yield is 10.0 grams.

Four (4.0) grams of the dried insoluble product are resuspended in 400 ml (10 mg/ml) of 0.488 M sodium acetate pH 6.9 with the aid of a Dounce homogenizer. The sodium acetate solution is immediately extracted three times with 200 ml each of a fresh aqueous phenol solution made as follows: 180 ml of 0.488 M sodium acetate pH 6.9 is added to a one pound bottle of crystalline phenol and mixed until a complete solution is effected. Each phenol extract is centrifuged for 30 minutes at $11,000 \times G$ at 4° in the Beckman J-21B to break the emulsion. The aqueous phases are pooled and extracted two (2) additional times with phenol solution in a similar manner. The phenol phases are discarded and the pooled aqueous phases (500 ml) are dialyzed at 4° for 22 hours with three 14.0 liter changes of glass distilled $H_2O$. The final dialysis ratio is 1:22,000 volumes. No trace of phenol odor is present in the final dialysate.

To the dialysate (500 ml) there is added 12.5 ml of 2.0 M CaCl$_2$ to a final concentration of 0.05 M CaCl$_2$. The solution is then brought to 75% ethanol with dropwise addition over 2-3 hours of 1,500 ml of 100% ethanol to the rapidly stirring solution. After standing 12-18 hours at 4° the resultant precipitate is collected by centrifugation in the Beckman J-21B at 27,000×G (15,000 rpm in the JA-20 rotor) at 4° for 30 minutes, washed two times with 100% ethanol and two times with acetone, and dried in vacuo over anhydrous CaCl$_2$ at 4°. The yield is 1.0 gram.

The dried material (1.0 g) is resuspended at 5 mg/ml in 200 ml of 0.05 M CaCl$_2$ and centrifuged at 100,000×G (40,000 rpm in the 50.2 Ti rotor) for 90 minutes at 4° in the Beckman L2-75 centrifuge. The clear supernatant fluid (195 ml) is decanted off the small glassine pellet and brought to 75% ehtanol with dropwise additiona of three volumes of 100% ethanol (585 ml ethanol) over a period of 2-3 hours, to the rapidly stirring solution. After standing 12-18 hours at 4° the precipitate is collected by centrifugation (27,000×G) washed two times with 100% ethanol, two times with acetone and dried in vacuo over anhydrous CaCl$_2$ at 4°. The yield is 802.0 mg. The pellet is discarded.

The dried material (785 mg) is resuspended in 180 ml of 0.05 M CaCl$_2$ (4.4 mg/ml and brought to 10% ethanol with dropwise addition of 20.0 ml 100% ethanol. The mixture is clarified immediately by centrifugation at 100,000×G (40,000 rpm in the 50.2 Ti rotor) for 90 minutes at 4°. The pellet is discarded and the clear supernatant fluid (194 ml) is brought to 75% ethanol by adding 505 ml of 100% ethanol. After stirring 2-3 hours the mixture is left at 4° for 12-18 hours to insure complete precipitation.

The polysaccharide precipitate is collected by centrifugation and washed two times with 100% ethanol and two times with acetone. After drying in vacuo over anhydrous CaCl$_2$, the yield is 724.63 mg of a polysaccharide having the following characterization:

| Ribose | = | 28.% | (Orcinol) |
|---|---|---|---|
| Nucleic acid | = | 0.8% | (Optical Density) |
| Protein | = | 1.0% | (Lowry) |
| Kav | = | 0.01% | (52%), 0.19 (48%) (Sepharose 4B) |
| TGA | = | 12.2% | |

Limulus (0.0005 γ/ml) = negative
Rabbit pyrogen (0.25 γ/kg) = negative
Immunodiffusion: No Con A reactivity (at 1.0 mg/ml)
Reaction of identity with polyribophosphate vs. anti-H. influenza type b (at 4.0 μg/ml)
Back-extrapolated theoretical yield = 2887.25 mg/200 liter fermenter, or 14.43 mg/liter of culture medium.

EXAMPLE 2

The purified polysaccharide is dissolved in PBS (phosphate buffered saline) at a concentration of 20 μg/ml and stored with a sufficient amount of phenol (preservative) at −20° C. until use. Children and infants are immunized by an intramuscular injection of 0.5 ml containing 10 μg of the purified polysaccharide. A booster injection of 0.5 ml also containing 10 μg of the purified polysaccharide is given intramuscularly four (4) weeks after the primary immunization.

EXAMPLE 3

The purified polysaccharide is dissolved in PBS (phosphate buffered saline) at a concentration of 100 μg/ml. The mixture is then sterile filtered and stored at −20° C. until use. Adults, especially females of child-bearing age (in order to protect offspring from neonatal meningitis caused by H. Influenza type b) are immunized by an intramuscular injection of 0.5 ml containing 50 μg of the purified polysaccharide.

What is claimed is:

1. An antigenic and immunogenic capsular polysaccharide from H. influenza type b consisting of about equal parts of ribose, ribitol and phosphate, substantially all of the polysaccharide having a molecular weight of at least about 5,000,000, and about half of the polysaccharide having a molecular weight of at least about 10,000,000.